Aug. 26, 1952 J. D. BROWNELL Plant Pat. 1,122
ROSE PLANT
Filed Aug. 3, 1951
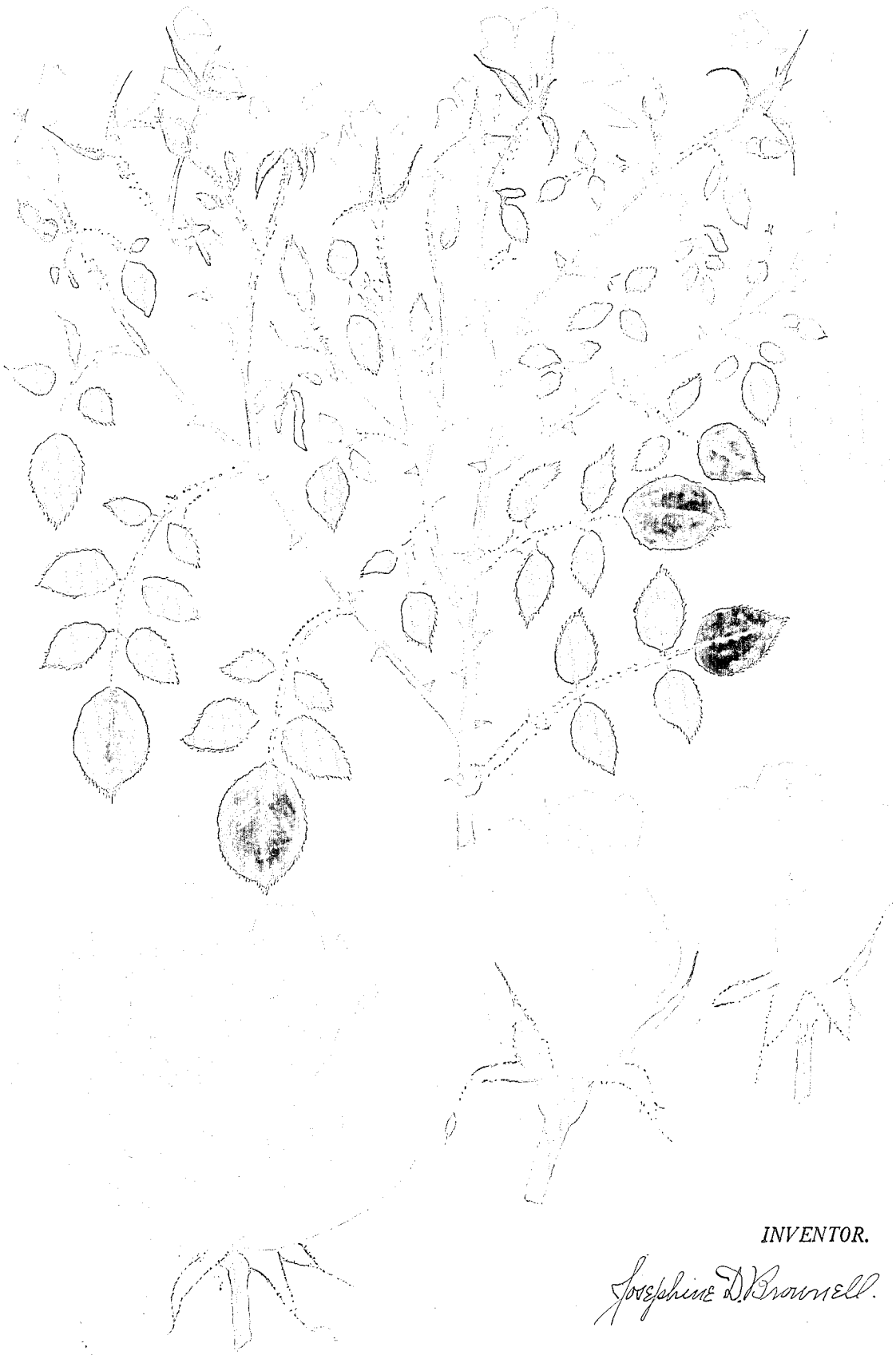
INVENTOR.
Josephine D. Brownell.

Patented Aug. 26, 1952

Plant Pat. 1,122

UNITED STATES PATENT OFFICE 1,122

ROSE PLANT

Josephine D. Brownell, Little Compton, R. I.

Application August 3, 1951, Serial No. 240,164

1 Claim. (Cl. 47—61)

My invention relates to rose plants and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States:

The red and yellow shades (ordinary dictionary definition) of its petals, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers, notable after early bloom time and until frost;

The intensity of its remontant and everblooming or reblooming character;

Its character of ascending in height by recurrent branching and progressively longer stems from the base;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by blackspot, under certain definite conditions of exposure, without any cultural control.

In the accompanying drawing forming a part of this specification I have shown my new rose in its natural colors; that is, as near as is possible to do so artificially.

A single detached petal is shown in color of outer and inner surfaces, the upper such view illustrates the inner petal surface.

My new rose is otherwise described as follows:

Type: Hybrid tea, *Rosa wichuraiana* hybrid, dwarf, for garden display, cut flower and forcing or growing under glass.

Class: Hybrid tea with sufficient bloom production to be classified also as of that commercial classification known as Floribundas, further restricted by originator to include only those varieties that can survive moderately low sub-zero temperatures.

Breeding: This variety was produced and bred by me and under my direction by propagation and cross pollenation.

It came into being as a seedling grown from a seed borne on "Pink Princess" (Plant Patent 859), and the pollen parent was "Shades of Autumn" (Plant Patent 542).

The pollenation that fertilized the seed that grew into my new rose was directed by me and was performed by emasculating flowers and placing thereon a bag protecting from self and foreign pollen. These bags were later removed and the flowers were hand pollenated with a camel's hair brush and the bags immediately replaced. The date of this pollenation was July 9, 1948.[1] The seed was planted under my direction on December 23, 1948, and the date of the first flower was August 13, 1949.

I have since made and directed extensive propagations and tests of this plant and flower.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1949–50 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one and frequently two or three or more on each stem, in the usual hybrid tea type of cluster except that well grown plants often produce stems three feet or more long with a terminal cluster up to twenty-five or more blooms on cluster branches of various lengths from about three inches up to about ten inches each with terminal blooms numbering one to five or more in a notable open form of cluster, after the manner illustrated in the drawing. The pedicels and peduncles are

[1] This and other dates herein are approximate.

medium small in diameter and medium in length, erect, stiff, almost smooth, free from large prickles and bristles but with a few very small prickles varying to small hairs. Stems are long, diameter medium to small and notably stiff and rigid.

Quantity of bloom: Free, being cumulative in quantity from year to year as the plant increases in size, flowering through the summer, plants well grown will after being planted one year produce over one hundred blooms.

Fragrance: Distinctive, pleasing China tea in combination with that of *Rosa wichuraiana*, under favorable environment.

Bud: Neck normal as described, opens well, being little to not at all affected by hot or wet weather or both, as to color and form, except at very high temperatures the color is less intense and the form of the petals is less recurled.

Before the calyx breaks the size is medium, form moderately pointed, frequently with one or more sepals having slight foliaceous parts extending beyond the apex of the calyx up to about one-eighth of an inch, the number and size of the foliaceous parts being variable, otherwise the sepals are usually normal and regular, tapering to lanceolate at their apex, turning back nearly perpendicular to the pedical as the bud opens, usually two of the five sepals have two very narrow short pointed appendages.

The entire plant is distinctive in that its entire expression of detail form is unusually irregular; as for example two opposing leaflets that normally are the same size and form occasionally differ in size in the ratio of one to five and with a similar ratio of width.

Color of the bud as the calyx opens and the flower begins to unfurl: outside of the outer petals, Nasturtium Orange at 610/2,[2] lower down to Yellow Ochre at o7/1 and lower portion to base of petal Chrome Yellow at 605/1, outer edges and entire surface irregularly stained, streaked and splashed by varying intensity of overlay of Orient Red from 819/3 to 819/1. Outer side of inner petals same except much less of the Orient Red.

Inner side of petals, top portions variable from Fire Red at 15/3 to Orient Red at 819/1 with lower portions Chrome Yellow at 605/1.

The demarkation between these two last named colors of Red and Yellow is notably irregular and pointed upward and downward.

The foregoing color descriptions are approximate and vary slightly.

Opening flower same, slowly softening to Persian Rose at 628/1 to 628 on inner side of petals and outer side to Peach at 512/1.

The flower usually varies in size around four inches in diameter, petals vary from twenty-five to forty, frequently with some smaller petals and petaloids in the center, variable in number.

The flower opens high centered, often informal when larger number of petals; recurled, with display of stamens early with few petals, later with many. The petals are variable from ovate to obovate to irregular, and the smaller petals and petaloids are often notably irregular. Texture is medium to thick; both sides brilliant. The time of opening in favorable conditions is four to five days.

The petals are substantial and after about

[2] Color references unless otherwise noted are to British Horticultural Colour Chart.

six to seven days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

Reproductive organs:

Stamens, quantity variable, being of medium average length and nearly even in length.

Anthers, Apricot 609/2. Filaments, Carrot Red 612/3. The last two mentioned colors are slightly variable.

Pistils are several of slightly uneven lengths, averaging around one-third inch long.

No hips or seeds have been noted.

Sepals are persistent and break off easily.

*Plant*

Foliage: Is abundant, of compound leaves of one to seven, the lesser number usually nearer the flower. Size of the leaflets notably variable, averaging about half way between the leaflets of *Rosa wichuraiana* and the leaflets of the average hybrid tea in commerce. The leaflets are thick and hard. Form of leaflets vary from ovate with apex moderately acute to nearly lanceolate throughout, bases from rounded to pointed, in some instances with the base out of alignment with the opposing leaflet one-sixteenth of an inch or more, margins with unusually fine pointed serrations. In some instances the opposing leaflet is not produced, in many instances an opposing leaflet is very much smaller and/or narrower than its mate.

Color of leaflets on the upper surface is approximately Spinach Green at o960, with reverse side Spinach Green at o960/3.

The rachises are medium, moderately narrow to slender, upper side smooth except some very short hairs on edges. Under side moderately smooth, usually three to five short prickles.

Stipules are about twice as long as normal and about one-half normal width. The appendages at the upper end are small, narrow and pointed and form an angle of about 90°.

Habit, dwarf, becoming bushy; upright, compact, more cumulative in growth from year to year than the normal hybrid tea rose plant, by stems from the base and by rebranching and growth and enlargement and extension of the stems from the base. The growth is moderately free at first, developing more rapidly after one year under favorable vegetative opportunity.

Color of mature stems is the same as that of the upper surface of mature leaves, shading on one side to color of under side of leaves.

Prickles, several, frequently two to four between leaves, averaging in length about one-quarter inch, shading from approximately Red color of inner side of petals to lighter at the base, turning lighter throughout and later to nearly colorless. Hairs few on upper portion of stems.

Winter resistance: A notable characteristic of this new rose is the resistance to moderate sub-zero temperature in combination with its hybrid tea character and its *Rosa wichuraiana* ancestry. This variety with grafted bud and plant above that bud entirely exposed above ground to mederate sub-zero temperatures survived and bloomed normally the following season. The word "temperature" herein refers to the Fahrenheit scale.

Comparisons: "Shades of Autumn" is the only bi-colored Wichuraiana hybrid tea known to us. My new rose is more brilliant and holds its color longer under exposure, the form of the bloom cluster is often much more open and produces many more blooms; the colors are slightly more intense, the petals are usually more recurled. The leaflets average much smaller.

The variety of non *Rosa wichuraiana* hybrid that most nearly resembles my new rose is probably "Forty-Niner" (Plant Patent 792); that blooms very much less in clusters of very many less blooms and the leaflets are very much larger.

I claim:

The new and distinct variety of Wichuraiana hybrid tea rose plant as described and illustrated, characterized by parti-colored red and yellow petals, the colors being brilliant and long lasting.

JOSEPHINE D. BROWNELL.

No references cited.